(12) United States Patent
Pickford

(10) Patent No.: US 6,261,625 B1
(45) Date of Patent: Jul. 17, 2001

(54) STABILIZATION OF MICROWAVE HEATED FOODS

(75) Inventor: Keith Pickford, Whitefield (GB)

(73) Assignee: Novus Foods Ltd, Whitefield (*) Notice: Subject to any disclaimer, the term of this patent is extended or adjusted under 35 U.S.C. 154(b) by 0 days.

(21) Appl. No.: 09/638,327

(22) Filed: Aug. 14, 2000

Related U.S. Application Data

(63) Continuation of application No. 09/000,319, filed as application No. PCT/GB96/01685 on Jul. 15, 1996, now abandoned.

(30) Foreign Application Priority Data

Jul. 15, 1995 (DE) .................................................... 9514542
Jul. 15, 1995 (DE) .................................................... 9514543

(51) Int. Cl.[7] .......................... A23L 1/0522; A23L 1/054
(52) U.S. Cl. ........................ 426/576; 426/578; 426/582; 426/654; 426/243; 426/246; 426/281
(58) Field of Search ............................... 426/95, 103, 243, 426/246, 324, 576, 578, 654, 582, 281

(56) References Cited

U.S. PATENT DOCUMENTS

| | | | | |
|---|---|---|---|---|
| H1229 | * | 9/1993 | McGinley et al. .................... | 426/654 |
| 4,948,608 | * | 8/1990 | Stypula et al. ........................ | 426/302 |
| 5,266,340 | * | 11/1993 | Samson et al. ......................... | 426/92 |
| 5,523,102 | * | 6/1996 | Morasch ................................ | 426/296 |
| 5,601,861 | * | 2/1997 | Gerrish et al. ........................ | 426/303 |
| 5,736,178 | * | 4/1998 | Cook et al. ............................ | 426/93 |

* cited by examiner

*Primary Examiner*—Nina Bhat
(74) *Attorney, Agent, or Firm*—Beyer Weaver & Thomas, LLP

(57) ABSTRACT

A microwave cookable or reheatable food material including a substrate foodstuff impregnated with a stabilizer composition adapted to increase in viscosity when irradiated in a microwave oven, and a method of stabilising a microwave cookable or reheatable food material including the step of impregnating the product with the stabilizer composition.

7 Claims, No Drawings

STABILIZATION OF MICROWAVE HEATED FOODS

This application is a continuation of U.S. application Ser. No. 09/000,319, filed Jan. 22, 1998, now abandoned, which claims benefit under 35 U.S.C. 371 of PCT/GB96/01685 filed Jul. 15, 1996.

This invention relates to foods products which can be cooked or reheated using microwave ovens. The invention relates particularly but not exclusively to foodstuffs comprising a core and a coating surrounding the core, for example a battered or breaded product. The invention also relates to non-coated food products and to ingredients for food products.

Many food materials for example natural muscle of poultry, fish or red meat and vegetable or processed foods contain a percentage of water. Most fresh foods contain more than 60% water. Some of this water is bound, that is tightly attached to the constituent cells. The remaining mobile water is available and can be frozen. Available water does not freeze at 0° C. because the dissolved solids lower the freezing point. At −30° C. virtually all available water is frozen. The rate at which foodstuffs are frozen is important because good quality is only obtained by quick freezing, with the best results being achieved by cryogenic freezing. If a food particle frozen to a core temperature of −30° C. is placed in a microwave oven, the microwaves will be primarily absorbed by the frozen available water. Whereas in conventional cooking heat is applied from the outside, in microwave cooking heat is generated from within and the process can be very rapid and quite violent. A consequence of this is to rapidly convert some of the available water to steam during the microwave cycle. After heating the foodstuff "rests" during which period there is a release of water which can drip from the product. This is particularly noticeable for example when heating frozen fish muscle. A microwave oven food product which is enrobed by a coating such as breadcrumb or pastry can become soggy and unpalatable.

Attempts have been made to limit the escape of moisture during microwave cooking by coating the product with a composition adapted to form an impermeable film. These attempts have been unsatisfactory because the natural distribution of water within the coated product can be lost. Furthermore an impenetrable coating or film detracts from the taste and mouth feel of the product.

According to a first aspect of the present invention a method of stabilising a microwave cookable or reheatable food material includes the step of impregnating the product with a stabiliser composition, the composition being adapted to increase in viscosity when irradiated in a microwave oven and being further adapted to decrease in viscosity after irradiation.

According to a second aspect of the present invention a method of stabilising a microwave cookable or reheatable food material including the step of impregnating the product with a stabiliser composition, the composition being adapted to increase in viscosity when irradiated in a microwave oven and being further adapted to decrease in viscosity after irradiation.

The product may be completely impregnated with the stabiliser composition so that the composition is distributed throughout the product. Alternatively the outer portions of the product may be impregnated to form a barrier preventing escape of moisture from the pore during irradiation.

The undesirable formation of an impermeable film is avoided.

A preferred method includes the steps of:
coating the product with a stabiliser composition;
placing the product in a container;
reducing the ambient pressure in the container to form a partial vacuum; and
releasing the vacuum to cause the composition to penetrate interstices of the product.

Alternatively the stabiliser may be impregnated into the food material by dusting onto the substrate surface, by soaking or by mixing the powdered composition into a finely divided or minced substrate.

A stabiliser composition in accordance with the present invention may comprise a reversibly thermogelling, water binding combination of starches, gums and optionally proteins. Preferred compositions include cellulose gum, hydrocolloid and protein isolate.

Suitable cellulose gums may be selected from: methyl cellulose, hydroxypropyl methyl cellulose and carboxymethyl cellulose. An amount of 4 to 50% is preferred, especially about 10 to 15%.

Suitable hydrocolloids may be selected from: alginates, xanthan gum, carageenan gum, gelatin, collagen, guar gum, dextrin, pectin, low methoxyl pectin and casein. Use of xanthan gum, guar gum or mixtures thereof is preferred. An amount of gum 1 to 25% may be used.

Suitable starches may be selected from: high amylose starch and modified starch. An amount of 5 to 40% is preferred.

Suitable protein isolates may be selected from: soya protein and an egg component for example egg albumen. An amount of up to 25% may be employed.

Preferred stabiliser compositions include polydextrose. Polydextrose is a randomly bonded condensation polymer of dextrose and polycarboxylic acids, for example citric acid which has been used as a bulking agent to replace sugars and fats in food compositions. Generally polydextrose comprises highly branched polymeric chains of dextrose wherein the 1–6 linkage predominates. Polydextrose may have a number average molecular weight between 1500 and 18,000. The use of polydextrose in foodstuffs is disclosed in WO96/00509. Use of a polydextrose variety sold under the trade mark LITESSE (Pfizer Inc) is preferred.

The proportions of ingredients used in the composition may vary dependent upon the nature of the substrate, particularly the total water content and available water content of the latter. It is important that the composition stabilises the water during microwave radiation yet does not cause the substrate to have any "off" flavours, odours or a poor mouthfeel. It is also important that the substrate is not too wet, too dry or have a slimy texture.

Stabiliser compositions in accordance with this invention may be used for coated products such as crumbed or pastry enrobed products. In addition the composition may be used for any uncoated products including cooked meats, for example sausages and fish. Vegetables and fruit may also be treated to make them physically stable and flavour retaining in a microwave oven environment.

Preferred embodiments of the invention provide a microwave cookable or reheatable food product comprising a stabilised microwave cookable or reheatable substrate as previously described coated with a microwave cookable or reheatable coating that becomes crisp after heating.

The coating may be formulated as disclosed in our copending PCT/GB96/00909.

The product may have a wide variety of configurations. One illustrative example is a pizza slice. In contrast to conventional pizza slices, the product may not incorporate a bread base to support the flavoured topping. In the present invention, the substrate is stabilised as previously described and then coated with a microwaveable coating. When flash fried the product becomes quite firm structurally, the configuration being maintained by the applied batter and crumb of the coating. The structural integrity of a product in accordance with this invention allows a pizza slice to be formed with a configuration of a segment, without the configuration being lost during cooking.

The invention is further described by means of examples but not in any limitative sense.

Proportions in this specification are by weight unless indicated otherwise. In the following examples the proportions may be selected within ranges where indicated to give a total of 100%.

Compositions comprising the following ingredients were prepared.

Example 1

| | |
|---|---|
| Cellulose gum (Methocel A4M) | 40% |
| Modified starch (Thermflo) | 40% |
| Xanthan gum | 15% |
| Guar gum | 5% |

Reformed cod was impregnated by coating followed by evacuation and release of the vacuum to cause the coating to penetrate interstices of the fish muscle. The composition described above can be used as a predust on fish.

Example 2

| | |
|---|---|
| Cellulose gum (Methocel A4M) | 35% |
| Modified starch (Thermflo) | 35% |
| Egg albumen | 10% |
| Xanthan gum | 15% |
| Guar gum | 5% |

This composition may be used for stabilisation of moist materials such as sauces, toppings, pizza topping, reformed fruit and the like.

Example 3

| | |
|---|---|
| Cellulose gum (Methocel A4M) | 25% |
| Modified starch (Thermflo) | 35% |
| Xanthan gum | 25% |
| Egg albumen | 15% |

This composition was a good stabiliser for reformed meat and fish. It was also satisfactory in pizza topping.

Example 4

| | |
|---|---|
| Cellulose gum (Methocel A4M) | 25% |
| Modified starch (Thermflo) | 40% |
| Xanthan gum | 25% |
| Modified Starch (Instant Clearjel) | 10% |

This composition was applicable where a more free flowing microwaveable sauce is required such as in chicken Kiev.

Example 5

| | |
|---|---|
| Vital wheat gluten (Tunnel VWG600) | 40% |
| Pectin (Hercules type D100 buffered) | 40% |
| Whole milk powder (Dairy Crest) | 20% |

This composition may be hydrated and mixed with a stabiliser in accordance with this invention and combined with a substrate, especially cheese products which consist substantially of cheese.

Example 6

| | |
|---|---|
| Cellulose gum (Methocel A4M) | 45% |
| Modified starch (Thermflo) | 20% |
| Xanthan gum | 8% |
| Egg albumen | 12% |
| Pea starch | 15% |

This composition may be added to a substrate as a dry powder. It has been found that the stabiliser compositions of Examples 5 and 6 in combination are effective when used with dairy products such as cheese either alone or in fills such as chicken Kiev. In addition these compositions may be used for microwaveable coated scrambled egg products.

The compositions of Examples 5 and 6 in combination for example in equal proportions afford microwave heatable cheese and dairy products. Previously cheese could not be microwaved without causing separation of the oil and solid components.

Example 7

| | |
|---|---|
| Cellulose gum (Methocel A4M) | 25% |
| Modified starch (Thermflo) | 40% |
| Xanthan gum | 10% |
| Egg albumen | 25% |

This composition may be used for stabilisation of meat and vegetable products both alone and also when mixed with the compositions of Examples 5 and 6. An amount of 2 to 6% preferably 5% can be used. An amount greater than 8% may be used for high water content substrates.

The previously described stabilisers form gels which strongly bind to water, retaining succulence in the food products. However a low freezing point is also desirable to minimise formation of ice crystals on storage. Use of compositions incorporating polydextrose have been found to afford remarkable results. Meat and poultry products have retained their texture and structure and high stabilisation of their water content.

Example 8

| | |
|---|---|
| Cellulose gum (Methocel A4M) | 4–20% preferably 12.5% |
| Modified starch (Thermflo) | 12–28% preferably 20% |
| Polydextrose | 42–58% preferably 50% |

-continued

| | |
|---|---|
| Xanthan gum | 1–7% preferably 5% |
| Egg albumen | 14–20% preferably 12.5% |

The proportions of the ingredients are selected within the above ranges to give a total of 100%.

An amount of 1 to 7% w/w of this mixture may be added to meat, fruit or vegetable products. The composition of Example 8 may be used to stabilise whole muscle of meat, poultry and fish. This composition is used by tumbling the whole meat particles in a tumble mixer with the powdered stabiliser composition in an amount of 1 to 7% by weight of the whole muscle material. The material may be tumbled for between 5 and 60 minutes to ensure complete adhesion of the stabiliser. The material is then subject to a strong vacuum of at least 7 bar which is then instantly released to absorb the stabiliser into the tissue.

The whole muscle may then be coated with a microwave-able coating, flash fried and frozen. When reheated in a microwave oven from frozen the product is stable and fully microwaveable. Alternatively whole muscle once stabilised can be fried for between 1 and 5 minutes at temperatures ranging from 180 to 200° C., cooled and then deep frozen. Reheating of the product affords a crisp texture and the moist succulence of a fresh deep fried product. In addition the freshly cooked flavour is retained and the whole muscle does not have the "reheated" flavour of some chicken products. Chicken drumsticks and spare ribs have a particularly good textured flavour.

Example 9

| | |
|---|---|
| Cellulose gum (Methocel A4M) | 17–27% preferably 22.5% |
| Modified starch (Thermflo) | 5–15% preferably 10% |
| Polydextrose | 45–55% preferably 50% |
| Xanthan gum | 1–8% preferably 4% |
| Egg albumen | 1–11% preferably 6% |
| Pea starch | 2–13% preferably 7.5% |

The proportions of the ingredients are selected within the above ranges to give a total of 100%.

The formulation of Example 9 can be used in conjunction with the composition of Example 5 in cheese, egg, butter and sauce mixes, as fillings, toppings or coated products to impart a very high degree of stability and moisture control. An amount of 2 to 10% preferably about 5% may be employed dependent on the moisture control of the substrate.

Example 10—Pizza Slice

| | % by weight |
|---|---|
| Liquid tomato (strained) | 56 |
| Seasoned tomato (pizza topping) | 26 |
| Tomato puree | 5 |
| Garlic | 5 |
| Oregano | 1 |
| Black pepper | 1 |
| Salt | 1 |
| Stabiliser of Example 8 | 5 |

-continued

| | % by weight |
|---|---|
| To 44 g of the above mixture 66 g of the following mixture was added | |
| Mozzarella cheese (grated) | 27 |
| Extra mature cheddar | 38 |
| Blue cheese (Stilton type) | 20 |
| Garlic sausage | 13 |
| Polydextrose | 2 |

The resultant mixture was placed in a high speed bowl chopper and thoroughly blended. The mixture was chilled to −3 to −5° C. and formed into slice shapes for coating.

The stabiliser may be added to the filling to give a total amount of 1 to 10%, preferably 4%. Following mixture of the pizza recipe and stabiliser, the combination may be formed in to a desired shape in a forming machine and then frozen to form stable shapes. Alternatively the mixture may be chilled to 0 to −10° C. before forming. The shapes, at a reduced temperature, for example 0 to −5° C. are preferably predusted with a predust formulation. A preferred predust formulation may comprise modified starch, albumin, protein and a mixture of gums. The predusted shapes are then coated by application of an aqueous mixture.

Preferred compositions are disclosed in PCT/GB96/00909 the disclosure of which is incorporated into this specification by reference.

A pizza filling was prepared from the ingredients as previously described. The ingredients were blended and then chilled to between −4° C. to −10° C. making the mixture plastic and not free flowing. The ingredients were fed into a forming machine and formed into slice shapes. The shapes were then coated with a predust. The shapes were fed by conveyor from the predust applicator into a batter applicator and coated. Thereafter they were fed into a crumb applicator. The fully coated particles were then flash fried at 190–200° C. for 40 to 60 seconds. The fried product was then cooled and frozen. Any method of freezing can be used but preferably cryogenic freezing using liquid nitrogen is employed. The frozen product is packaged in impermeable packs, preferably made from polypropylene and gas flushed with nitrogen. The product was stored at −20° C. or below.

The product can be reheated in a domestic or commercial microwave oven in their containers if the latter are for use in a microwave oven.

The enzyme additive comprised α-amylase (Novamyl) with additional neutrase and β-glucanase.

The batter was prepared by placing the starch into a mixer, dispersing the gum, emulsifiers, enzyme additive and sugar into the mixture, followed by addition of the egg and flour and further mixing to ensure complete dispersion. The batter was packaged in moisture proof containers for storage before use.

The powdered batter mixture (1 part) was added to water (3 parts) or less water according to the desired viscosity of the batter.

The pH of the batter mix was 4.5 to 5.0.

A pizza filling was prepared from conventional ingredients.

The predust used was:

| Novatex PT | % by weight |
|---|---|
| Modified starch (Thermflo) | 35 |
| Methyl cellulose (methocel A4M) | 25 |
| Xanthan gum | 25 |
| Egg albumen | 15 |

A preferred coating may incorporate the following ingredients by dry weight

| | | |
|---|---|---|
| (i) | starch, preferably high amylose starch | 30–60% |
| (ii) | cellulose gum | 1–5% |
| (iii) | flour | 25–60% |
| (iv) | an enzyme additive, and | balance to 100% |
| (v) | ancillary ingredients, including one or more emulsifiers and one or more reducing sugars | | wherein the enzyme additive comprises one or more alpha-amylases optionally together with one or more further enzymes, buffers and stabilisers.

The enzyme additive comprised

| | % by weight |
|---|---|
| Glucono-D-lactone | 18 |
| Sodium Acid pyrophosphate (pH - 4.2) | 10 |
| Mono sodium phosphate (pH - 4.5) | 50 |
| Ammonium bicarbonate | 19 |
| α-Amylase (Novamyl) | 3 |

Use of the enzyme additive has the advantage that use of soya flour is not essential. A mixture of soya flour and other flour, for example wheat, rye, oats, buckwheat, maize, rice or potato flour may be employed. Alternatively the soya flour may be replaced entirely with one or more other types of flour. The flour may be selected to provide a range of flavours which were not previously available. Gluten free flours are preferred. The enzyme additives may be selected in accordance with flour employed.

The starch may comprise high amylose starch. Alternatively or in addition pea or maize starch may be employed.

A preferred coating comprises the following ingredients by dry weight:

| | |
|---|---|
| high amylose starch | 35–50% |
| guar gum | 1–5% |
| cellulose gum | 1–5% |
| glyceryl monostearate or other emulsifier | 1–3% |
| whole egg | 5–20% |
| D-xylose or other reducing sugar | 1–5% |
| dextrose | 1–5% |
| flour | 30–50% |
| an enzyme additive, and ancillary ingredients | balance to 100% |

Preferred alpha amylases include maltogenic amylases including those expressed by Bacillus subtilis strains. A preferred enzyme additive is available under the Trade Mark Novamyl MG manufactured by Novo Nordisk. Preferred enzyme additives act on the starch fraction of flour, modifying the starch to create low molecular weight sugars eg amylose and dextrins which improve the water retention capacity of the batter. However Novamyl amylases reduce any tendency to retrogradation or undesirable further hydrolysis during cooking or reheating.

Additional enzymes may include proteases for example endopeptidases such as Alkalase manufactured by Novo Nordisk; pentosanase, for example Pentopan 200 MG manufactured by Novo Nordisk and metaloproteases, for example Neutrase manufactured by Novo Nordisk. Beta glucanases or other proteases serve to degrade polypeptides such as gluten during incubation of the batter.

Conventional buffers may be employed although use of phosphates is especially preferred. Preferred additives also incorporate glucono-d-lactone. The stabiliser may be ammonium bicarbonate although alternative stabilisers may be employed. Ammonium bicarbonate is preferred because it also serves to reduce undesirable odours.

Emulsifiers which may be used may comprise one or more of the following: glyceryl monostearate, lecithin, milk powder, dried whole egg, dried egg white and dried egg yolk. Use of lecithin is especially preferred to optimise fluid properties and emulsion stability of the batter. Especially preferred compositions incorporate mixtures of egg, glyceryl monostearate and lecithin. Preferred lecithins include soya lecithin filtered and a low iron soya lecithin, activated soya lecithin, lyso-lecithin and phosphatidylchoine.

The reducing sugar is preferably D-xylose. Alternative reducing sugars which may be employed instead of or in addition to xylose are xylitol, sorbitol and L-rhamnose.

The coating compositions are preferably blended by mixing under high shear, followed by being allowed to stand for about one hour. Heat generated during mixing promotes enzyme activity. A preferred method includes mixing at a rate to cause heating to 30 to 60° C.

Example 11—Chicken Nuggets

| | % by weight |
|---|---|
| Breast meat | 35 |
| Thigh meat | 35 |
| Skin | 6 |
| Water | 12 |
| Stabiliser of Example 8 | 5 |
| Rusk | 5 |
| Salt | 2 |

The chicken meat was coarsely minced and the chicken skin emulsified in a bowl chopper. The meat and skin were combined in a paddle mixer or tumble mixer along with water and salt.

A stabiliser was added and mixed gently. The rusk was added and the mixture was chilled to between −5 to −10° C. and formed into shapes for coating.

Example 12—Fish Nuggets

| | % by weight |
|---|---|
| Cod | 93 |
| Salt | 2 |
| Stabiliser of Example 8 | 5 |

Fresh or fully thawed cod or other white fish was used. Seasoning was optional but it was found that when using a seasoning the amount of the stabiliser could be reduced. The fish muscle was tumbled in a tumble mixer or paddle mixer to retain as much tissue integrity as possible and the salt was added. Tumbling was continued until the size of the pieces was reduced. The stabiliser was added and the mixture was further tumbled until a stable tissue mixture was formed. The mixture was allowed to stand for 30 min, chilled to −2 to −5° C. and formed into the desired shapes for coating.

Example 13—Fruit crunchies

|  | % by weight |
|---|---|
| Diced Bramley apple | 90 |
| Lemon juice (concentrated) | 4 |
| Granular citric acid | 1 |
| Stabiliser of Example 5 | 5 |

The fruit, lemon juice and citric acid were mixed as gently as possible to retain as much of the apple structure as possible. The stabiliser was added and gently mixed until the texture stiffened. The mixture was allowed to stand for 30 min to 1 hour, chilled to −4 to −5° C. and formed.

Example 14—Breakfast Brunch Bar

|  | % by weight |
|---|---|
| Pasteurised scrambled egg | 73 |
| Stabiliser of Example 5 | 2.5 |
| Stabiliser of Example 6 | 2.5 |
| Polydextrose | 2 |
| Cooked bacon | 20 |

The stabiliser of Example 5 (20%) was mixed with water (80%) using a high shear mixture. The egg was placed in a tumble mixer and the stabiliser mixture added to it. Tumbling was continued and the stabiliser of Example 6 was added together with the polydextrose and the cooked bacon. The mixture was tumbled until it stiffened, chilled to −4 to −5° C. and formed into shapes for coating.

Any other material may be used in place of the cooked bacon including prawn, mushroom, sausage, garlic sausage, cheese, vegetable and pineapple.

Example 15—Mini Burgers

|  | % by weight |
|---|---|
| Minced pork | 74.5 |
| Pinhead rusk | 5 |
| Salt | 1.5 |
| Water | 12.5 |
| Pork flavouring | 1.5 |
| Stabiliser of Example 8 | 5 |

Minced pork was placed in a tumble or paddle mixture and salt and water added. The mixture was mixed gently and the stabiliser added followed by the rusk. When the mixture stiffened it was allowed to stand for 30 min to 1 hour, chilled to −4 to −5° C. and formed into shapes for coating. Burgers in accordance with this example may also be made from beef, pork and lamb using appropriate seasonings. For example lamb burgers may incorporate mint sauce or fruit flavours and pork burgers can incorporate apple or stuffing.

Example 16—Cheese Nuggets

|  | % by weight |
|---|---|
| Mozzarella cheese | 50.5 |
| Extra mature cheddar | 30 |
| Modified Starch (Thermflo) | 5 |
| Stabiliser of Example 6 | 5 |
| Stabiliser of Example 5 | 5 |
| Garlic puree | 2 |
| Polydextrose | 1 |
| Salt | 1 |
| White pepper | 0.5 |

The mozzarella and cheddar cheese were placed in a bowl chopper and chopped to a coarse mixture. The stabiliser of Example 5 was made to a 20% solution in water and added to the cheese along with the other ingredients. The mixture was chopped until a fine stiff emulsion was formed, chilled to −4 to −5° C. and formed. These nuggets can be formed incorporating chives, onion, herbs and flavours as desired along with various types of cheese.

These nuggets do not melt when deep fried or microwave heated. The cheese product of this Example can also be used as a filling for Kievs, potatoes and other products.

It will be evident from the foregoing examples that a wide variety of substrates can be stabilised in accordance with this invention without loss of texture, structure or flavour. Other products include sausages, potato products, vegetable nuggets and burgers, kebabs and kebab meat. The formed pieces can be flash fried as a cooked product which can be reheated from frozen using a microwave oven. The products may also be coated with a microwaveable coating.

The coating process includes the steps of predust application, batter application, crumb application, flash frying, freezing and packaging.

The shapes at reduced temperature, for example −5 to −10° C. are preferably predusted with a predust formulation. A preferred predust formulation may comprise modified starch, egg albumen, protein, sugars and a mixture of gums.

Examples 17 to 21 illustrate coating compositions which may be used with food products which have been stabilised as previously described.

Example 17

The following coating formulation was employed.

|  | % by weight |
|---|---|
| High amylose starch | 35 |
| Cellulose/guar/xanthan gums | 3 |
| Dried whole egg | 10 |
| D-xylose or other reducing sugar | 2 |
| Enzyme additive | 5 |
| Buckwheat or wheat flour | 20 |
| Wheat flour | 20 |
| Lecithin | 5 |

Example 18

| | % by weight |
|---|---|
| High amylose maize starch | 46.2 |
| Soya flour | 30 |
| Dried whole egg | 12 |
| Xanthan gum | 0.4 |
| Guar gum | 1 |
| Lecithin | 3 |
| α-amylase | 0.8 |
| Protease | 0.6 |
| Tetra sodium pyro phosphate | 2 |
| Dextrose | 4 |

Example 19

| | % by weight |
|---|---|
| High amylose starch | 48 |
| Guar gum | 0.5–2 |
| Glyceryl monostearate | 1 |
| Dried whole egg | 13 |
| D-xylose | 2 |
| Enzyme additive | 3 |
| Soya flour | balance to 100 |

Example 20

| | % by weight |
|---|---|
| High amylose pea starch (min 65%) | 45 |
| High amylose maize starch | 7 |
| Soya flour | 32 |
| Dried whole egg | 12 |
| Glyceryl monostearate | 2 |
| α-amylase | 0.5 |
| Xanthan gum | 0.2–1 |
| Modified starch (Thermflo) | balance to 100 |

Example 21

| | % by weight |
|---|---|
| High amylose starch (Microcrisp, National starch) | 48 |
| Guar gum (Red Carnation) | 1 |
| Methocel A4M (Dow (fat barrier)) | 0.25 |
| Glyceryl monostearate (Emuldan, Grinstead) | 2 |
| Whole egg (Henningsens, W1) | 14 |
| D-xylose | 2 |
| Enzyme additive | 3.75 |
| Soya flour (Hisoy, ADM) | 29 |

The mixture (250 g) was added to water 750 g) at 11° C. and mixed for 25 min using a Silverson high shear mixer until the temperature was greater than 40° C. The viscosity readings using a number 3 spindle at 12 rpm were as follows

| TIME | INITIAL | 1 HOUR | 2 HOURS |
|---|---|---|---|
| Viscosity/cp | 570 | 610 | 1580 |
| Temperature/° C. | 40 | 30 | 26.9 |

What is claimed is:

1. A microwave cookable or reheatable food material comprising a substrate foodstuff impregnated with a stabilizer composition, comprising:

| | |
|---|---|
| cellulose gum | 4–20% |
| modified starch | 12–28% |
| polydextrose | 42–58% |
| xanthan gum | 1–7% |
| egg albumen | 4–20% | with the proviso that the amounts of ingredients are selected to give a total of 100%;

the composition being adapted to increase in viscosity when irradiated in a microwave oven.

2. A material as claimed in claim 1, wherein the cellulose gum is selected from the group consisting of methyl cellulose, hydroxypropyl methyl cellulose and carboxymethyl cellulose.

3. A composition as claimed in claim 1 wherein:

| | |
|---|---|
| cellulose gum | 12.5% |
| modified starch | 20% |
| polydextrose | 50% |
| xanthan gum | 5% |
| egg albumen | 12.5% |

4. A material as claimed in claim 1 wherein the substrate foodstuff is wholly or substantially cheese.

5. A material as claimed in claim 4, wherein the stabilizer further comprises a mixture of gluten, pectin or whole milk powder.

6. A method of stabilising a microwave cookable or reheatable food material product including the step of impregnating the product with a stabiliser composition, as claimed in claim 1, the composition being adapted to increase in viscosity after irradiation.

7. A method as claimed in 6, including the steps of coating the product with the stabilizer composition, placing the product in a container; reducing the ambient pressure in the container to form a partial vacuum; and releasing the vacuum to cause the composition to penetrate interstices of the product.

* * * * *